United States Patent [19]

Skeppmark et al.

[11] Patent Number: 5,505,617
[45] Date of Patent: Apr. 9, 1996

[54] COLLETED ADJUSTABLE FLAT DENTAL TOOL

[75] Inventors: Henry Skeppmark, Jakobsdalsyagen, Sweden; Bernard Weissman, New York, N.Y.

[73] Assignee: Dentatus AB, Sweden

[21] Appl. No.: 195,791

[22] Filed: Feb. 14, 1994

[51] Int. Cl.⁶ .................. A61C 1/07; A61C 3/03
[52] U.S. Cl. .................. 433/118; 433/125; 433/134; 433/165; 433/166
[58] Field of Search .................. 433/82, 165, 166, 433/127, 129, 118, 119, 125, 134

[56] References Cited

U.S. PATENT DOCUMENTS

| | | |
|---|---|---|
| 1,821,079 | 9/1931 | Schultze . |
| 3,967,380 | 7/1976 | Malata et al. . |
| 4,526,541 | 7/1985 | Hubschmid .................. 433/165 |
| 4,571,184 | 2/1986 | Edwardson .................. 433/166 |
| 4,834,653 | 5/1989 | Edwardson .................. 433/118 |
| 4,954,082 | 9/1990 | Weissman .................. 433/80 |
| 4,976,625 | 12/1990 | Weissman .................. 433/118 |
| 4,984,985 | 1/1991 | Edwardson .................. 433/123 |

FOREIGN PATENT DOCUMENTS

| | | | |
|---|---|---|---|
| 155090 | 12/1920 | United Kingdom | .................. 433/118 |

*Primary Examiner*—Cary E. O'Connor
*Attorney, Agent, or Firm*—Paul J. Sutton; Barry G. Magidoff

[57] ABSTRACT

A dental implement designed to be retained for reciprocating-movement by the sleeve member of a dental handpiece. The dental implement is comprised of a flat dental tool having a flat blade portion and a flat shank portion. The flat blade portion can also be formed with a triangular or arcuate cross-section while retaining the flat shank portion and the blade edges can be straight or have a saw-tooth configuration. A removable tool holder has a slot to receive the dental tool and a outside cylindrical shape complementary with the bore of the sleeve member. Forces applied to the tool holder control the displacement of locking protrusions on the tool shank to selectively permit the tool to be driven in a reciprocating movement with or without rotation and to be removed entirely from the sleeve member.

31 Claims, 8 Drawing Sheets

FIG.12
FIG.14
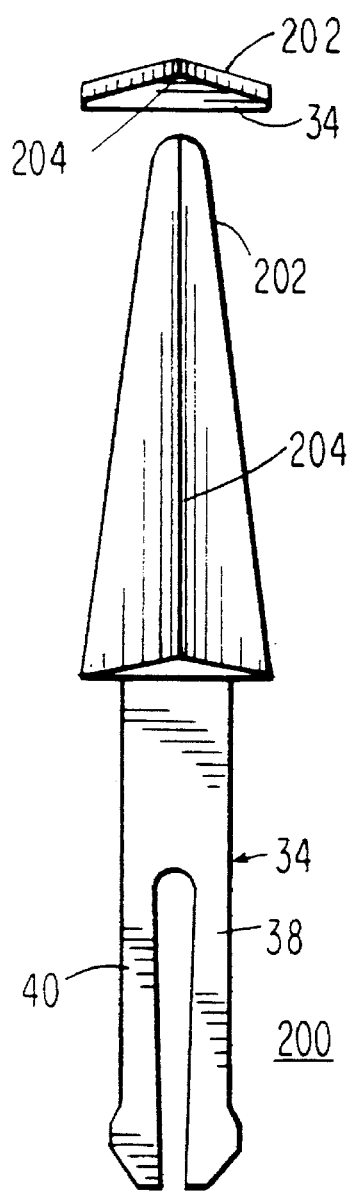
FIG.11
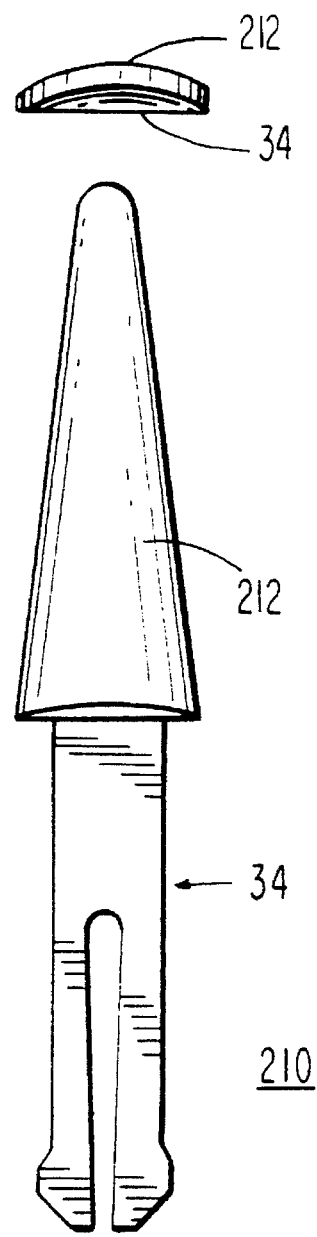
FIG.13

COLLETED ADJUSTABLE FLAT DENTAL TOOL

BACKGROUND OF THE INVENTION

1. Field of the Invention

The present invention relates to a dental implement which can be retained and reciprocatingly driven by the sleeve of motor-driven, reciprocating dental tool and more particularly to a dental implement which can be formed of flat stock and adapted for use in a dental tool by means of a removable tool holder.

2. Description of the Prior Art

Presently used dental implements are complex and require many operations for their production. The lower portion of such dental implements may be flat but the upper portion required to mate with the driven sleeves of present dental handpieces must provide a generally circular configuration in cross-section.

In U.S. Pat. No. 3,967,380 issued Jul. 6, 1976 tools 7 and 27 have round solid shanks 7a and 27a to mate with tool holders 2 and 22.

U.S. Pat. No. 4,526,541 issued Jul. 2, 1985 shows a dental implement 1 formed of flat stock with a flat blade 3 and a shank or holding part 2 formed with a pair of opposed, bowed ears 2a having the form of a not completely closed cylinder.

U.S. Pat. No. 4,571,184 issued Feb. 18, 1986 shows a dental implement having a split, solid, cylindrical shank 1 and a flat spatula-like portion 2.

In U.S. Pat. No. 4,834,653 issued May 30, 1989, the solid, cylindrical shaft end portion 7 of tool 1 has a groove 8 which receives spring ring 11 to lock tool 1 in place.

Weissman U.S. Pat. No. 4,954,082 issued Sep. 4, 1990 and owned by the Applicant hereof shows, in FIGS. 10 to 13A, a file tool 104 formed of stainless steel sheet material with a flat blade portion 106 and a shank 110 formed into a complete hollow cylinder as shown by FIGS. 10 to 13 or into a complete, hollow cylinder by forming an S-pattern as shown by FIG. 13A.

Similarly, in Mr. Weissman's U.S. Pat. No. 4,976,625 issued Dec. 11, 1990 the tool 4 has a blade with a molded cylindrical sleeve-shank 100.

U.S. Pat. No. 4,984,985 issued Jan. 15, 1991 shows a dental tool with a flat blade and a solid, cylindrical shank 15 with a slot 151 therein to allow the shank to pass through a restricted bore.

In each of these prior art patents the dental implement or tool has a flat blade and a cylindrical shank to mount the implement or tool in the driven sleeve in a reciprocally driven dental hand piece. The tool can be made of round stock with the blade formed into a flattened shape by secondary operations such as forging, swagging, coining etc. Alternatively, the shank can be made of round stock and a flat blade joined to it. The shank can be made more compliant by forming a slot therein. Finally, the dental implement or tool can be made of flat stock and the shank formed into a cylindrical shape by bending the marginal edges of the shank into a complete or incomplete cylinder or forming a cylinder by bending the marginal edges in an S-shaped configuration.

Regardless of the technique employed, the dental implement or tool can only be formed by a great number of operations and because of the size of the dental implements and tools, the machines used to form them must be high precision equipment.

SUMMARY OF THE INVENTION

The present invention overcomes the difficulties and problems which exist in the prior art by forming a dental implement or tool as an easily formed flat device having a flat blade and a flat shank and a removable tool holder which allows the flat device to be retained and reciprocally driven by a dental handpiece.

More particularly, the tool can be stamped from flat stock. The blade portion has two flat faces, one or both of which can be coated with an abrasive material. The shank portion is formed with two arms separated from each other by a relief slot, so that the arms can be moved closer to one another to decrease the width of the shank. Protuberances are placed on the outer edges of the arms to control the reciprocation and rotation of said tool with respect to the sleeve of a handpiece. If desired the blade portion can be made to have an arcuate or triangular cross-section while the shank retains its flat cross-section.

The removable tool holder has a cylindrical body terminating in a tapered portion and an enlarged head. A slot goes through most of the body and is wide enough to receive the tool shank therein in an interference fit. The slot extends into the tapered portion to permit the protuberances of the shank to extend beyond the holder diameter at that point.

The slot is fully open at the holder end remote from the enlarged head and is formed as a V-shaped recess adjacent the enlarged head end. The ends of the arms of the shank portion have a shape complementary to that of the recess. Depending upon the extent of the engagement of the recess with the ends of the shank arms, the separation of the arms and the extent of projection of the protuberances beyond the tool holder outer surface can be controlled.

The protuberances thus engage various recesses or the walls of the bore of the sleeve of the handpiece to determine the movement of the dental implement. It is therefore an object of this invention to provide a novel dental implement.

It is an object of this invention to provide a novel dental implement out of flat stock and not requiring multiple or complex mechanical operations.

It is still another object of this invention to provide a dental tool made entirely of flat stock and adapted to the bore of the sleeve of a dental handpiece by a tubular adapter.

It is yet another object of this invention to provide a dental tool made entirely of flat stock and adapted to the bore of the sleeve of a dental handpiece by a cylindrical adapter and which controls the interaction between the dental implement and the dental handpiece based upon the relative position of said adapter and said tool.

Other objects and features of the invention will be pointed out in the following description and claims and illustrated in the accompanying drawings, which disclose, by way of example, the principles of the invention, and the best mode which is presently contemplated for carrying it out.

BRIEF DESCRIPTION OF THE DRAWINGS

In the drawings in which similar elements are given similar reference characters:

FIG. 11 is a front elevational view of a modification of the tool of FIG. 1.

FIG. 12 is a top plan view of the tool of FIG. 11.

FIG. 13 is a front elevational view of a further modification of the tool of FIG. 1.

FIG. 14 is a top plan view of the tool of FIG. 13.

DESCRIPTION OF THE PREFERRED EMBODIMENT

Figure 1:
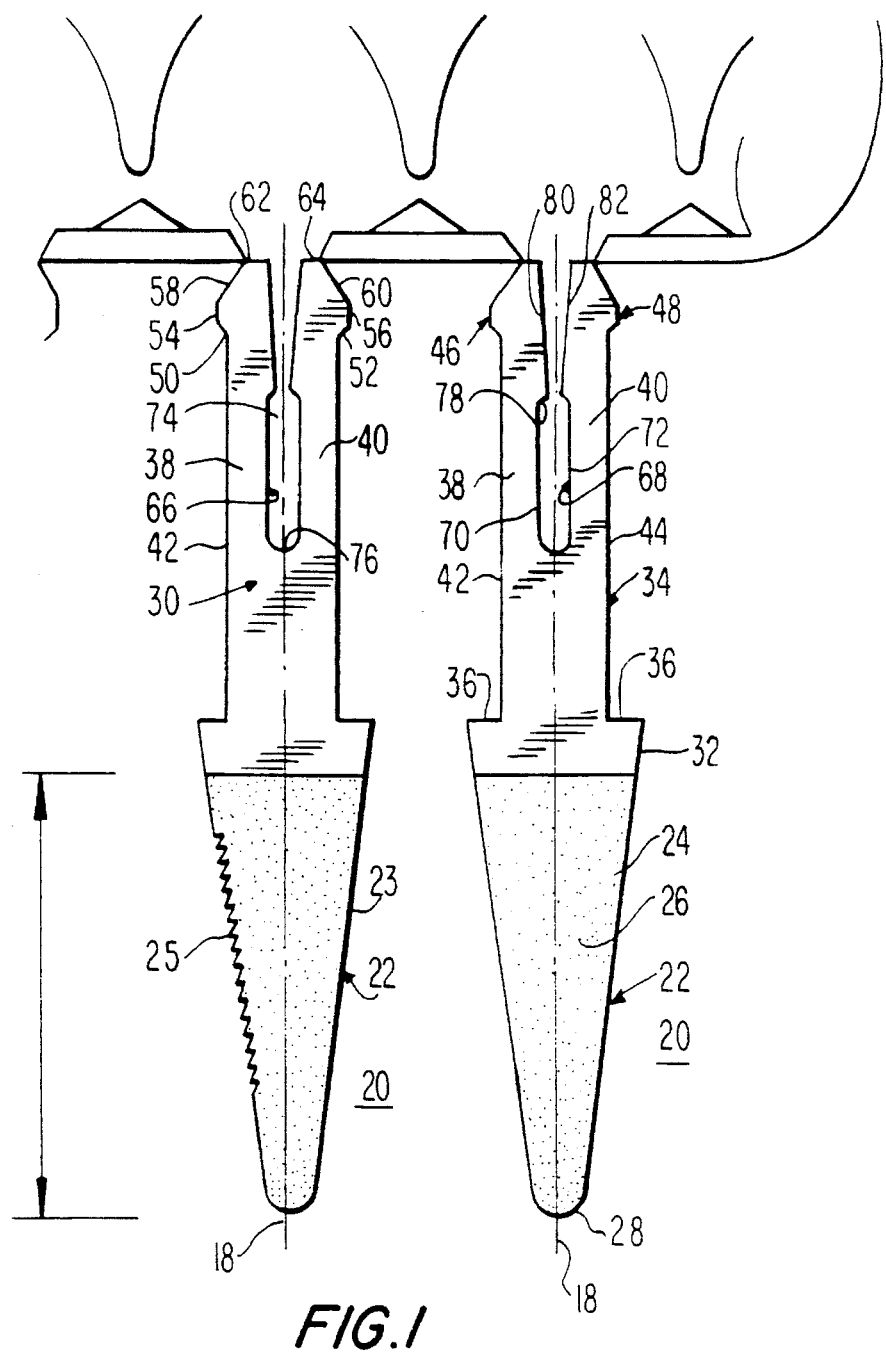
FIG. 1 is a front elevational view of dental tools according to the concepts of the instant invention on a runner after same have been stamped from a sheet of suitable flat stock.
Figure 2:
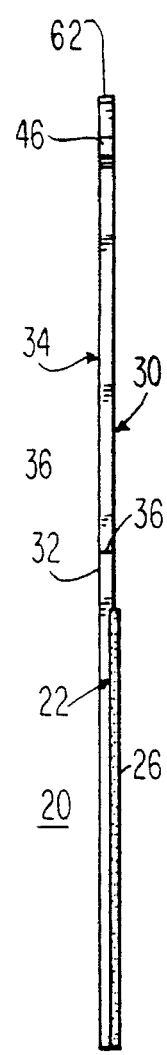
FIG. 2 is a side view of a dental tool of the type shown in FIG. 1.
Figure 5:
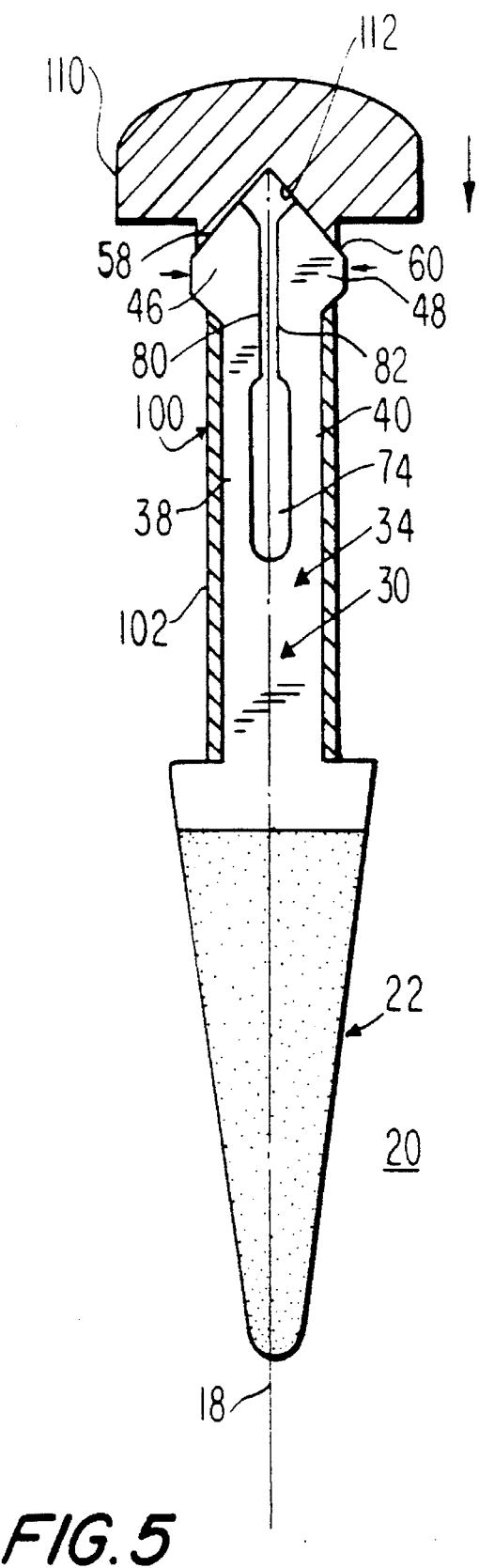
FIG. 5 is a front elevational view of the dental tool of FIG. 1 engaged with the recess in the enlarged head of the removable tool holder, the portion of the tool holder body in front of the tool having been removed to better appreciate the details of the dental tool.

Turning now to FIGS. 1, 2 and 5, a dental tool portion 20 of a dental implement constructed in accordance with the concepts of the invention is shown. Tool 20 can be punched out of a flat sheet of strong material such as stainless steel. Tool portion 20 has a blade 22 with two flat faces 24 at least one of which is covered by an abrasive material 26. The abrasive material 26 can be adhered to face 24 by the use of adhesives, bonding, brazing or the like depending upon the particular adhesive material chosen. Blade 22 is generally of a triangular shape with a rounded point 28. The marginal edges of blade 22 can be straight as at 23 or be formed as a saw-tooth cutting edge as at 25. If desired the blade 22 can be given cross-sections other than flat while retaining shank portion 30 flat. For example in FIGS. 11 and 12, the blade 202 of tool 200 is bent about its center 204 to give a triangular cross-section. The blade can also be formed into an acruate cross-section as shown in FIGS. 13 and 14 where tool 210 has its blade portion 212 formed into an arcuate configuration. Blade 22 is integral with shank portion 30 at base 32 of the shank portion 30 which continues the shape of the blade portion 22. The width of the major portion 34 of shank portion 30 is narrower than base 32 resulting in a shoulder 36 at each end of base 32. The portion 34 of shank portion 30 is further divided into two arms 38, 40 which are mirror images of each other.

Each of the two arms 38, 40 has an outer edge 42, 44, respectively, which are generally parallel to each other and terminate in the protrusions 46, 48, respectively. Protrusion 46 has a first portion 50 which extends outwardly from a central longitudinal axis 18, to a portion 54 parallel with axis 18 followed by portion 58 which extends back towards axis 18 and ending in portion 62 perpendicular to said axis 18. Similarly, protrusion 48 has a first portion 52 which extends outwardly from a central longitudinal axis 18, a portion 56 parallel with axis 18, a portion 56 parallel with axis 18 and a portion 60 which extends back towards axis 18 and ending in portion 64 perpendicular to the axis 18.

The arms 38, 40 also have an inner edge 66, 68, respectively made up of the walls 70, 72 which are defined by slot 74 centered about the axis 18 and with a rounded bottom area 76 to prevent the development of stress in shank portion 34 as a result of the flexing of arms 38, 40. From top area 78 the inner edge 66 has an outwardly directed portion 80 which diverges from axis 18 and meets portion 62 of arm 38. An outwardly directed portion 82 meets portion 64 of arm 40.

Turning now to FIG. 5 the manner in which the arms 38 and 40 of dental tool portion 20 are operated will now be set forth. The removable tool holder 100, which will be described in greater detail below, has a generally cylindrical body 102 which at its second end 106 terminates in an enlarged head portion 110. A slot 112 through body 102 extends up to the enlarged head portion 110. At the joint of the body portion 102 and the enlarged head portion 110 is formed a recess 113 which has a profile which is complementary to surfaces 58 and 60 of arms 38 and 40. With no force applied to head portion 110, the arms 38 and 40 remain separated as shown by FIG. 1. As force is applied to head portion 110 downwardly, in the direction of blade 22, the action of the recess 113 upon the inclined surfaces 58 and 60 is to force the arms 38, 40 closer together causing the protrusions 46, 48 to move closer to axis 18 as shown by FIG. 5. A release of the force applied to head portion 112 will permit the arms 38, 40 to resiliently return to their original position as shown in FIG. 1.

Figure 4:
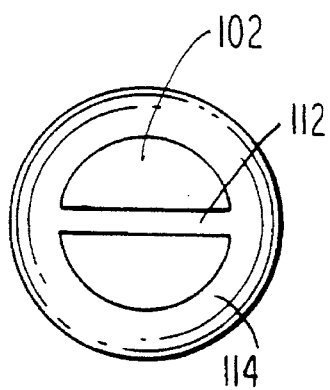
FIG. 4 is a bottom plan view of the removable tool holder of FIG. 3 with the dental tool removed.
Figure 3:
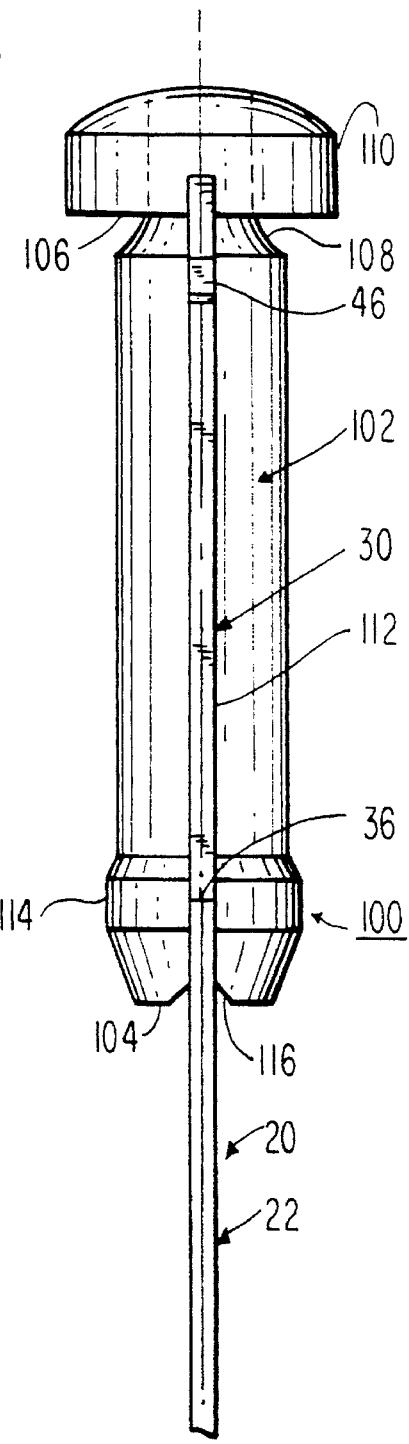
FIG. 3 is a side elevational view of a removable tool holder according to the concepts of the invention and with a dental tool positioned therein.

FIGS. 3 and 4 show the construction of the removable tool holder 100. Tool holder 100 has a generally cylindrical body 102 extending from a first end 104 to a second end 106. A slot 112 extends through substantially the entire body 102 opening at first end 104 and closed by enlarged head portion 110 adjacent second end 106. The second end 106 is tapered to permit a portion of the protrusions 46, 48 to project beyond the outer surface of body 102 at the tapered area.

The width of slot 112 is about the same as the thickness of the shank 30 of tool portion 20 to create an interference fit to prevent the tool portion 20 being dislodged from slot 112 of tool holder 100. To increase the holding power of tool holder 100, a collar 114 is placed about body 102 adjacent first end 104. This collar 114 with a tool 20 in place in slot 112 creates increased contact with the bore of the sleeve of a dental handpiece to prevent separation of the tool 20 from the tool holder 100. The entry to slot 112 is chamfered as at 116 to make insertion of a tool 20 into slot 112 easier.

Figure 9:
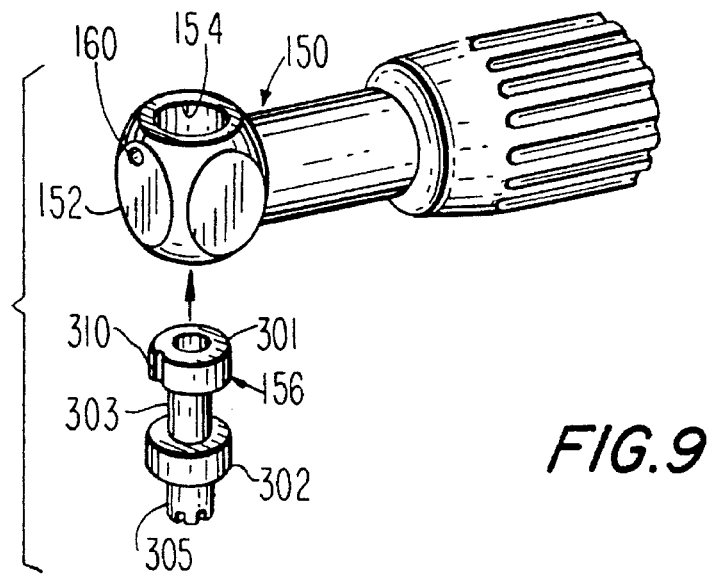
FIG. 9 is a fragmentary front perspective and exploded view of a dental handpiece and the tool drive sleeve and is FIG. 1 of U.S. Pat. No. 4,976,625 issued Dec. 11, 1990.

FIG. 9 shows the handpiece 150 from U.S. Pat. No. 4,976,625. Head 152 has a bore 154 therethrough in which is placed a motion-converting tool holder sleeve 156. Sleeve 156 is locked into head 152 by a steel ball, inserted in aperture 160, which engages slot 310 of sleeve 156. Upper and lower flanges 301 and 302 define a drive zone 303 between them. As set forth in the patent, the end of an eccentric drive shaft (not shown) rides in zone 303 and contacts flanges 301 and 302 to describe a reciprocating motion for sleeve 156. Engagement of the shaft with flange 301 drives sleeve 156 upwardly in FIG. 9 and engagement with flange 302 drives sleeve 156 downwardly in FIG. 9. A notched rim portion 305 will engage the tool 20 under certain conditions to prevent its rotation.

Figure 10:
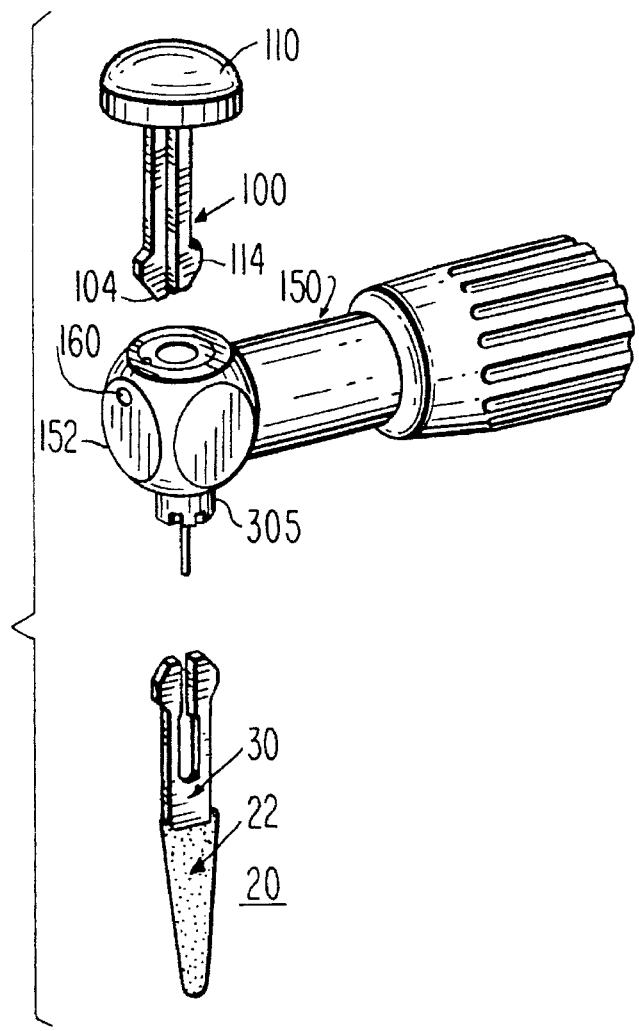
FIG. 10 is a fragmentary front perspective and exploded view of a dental handpiece with a tool drive sleeve in place and showing a dental implement according to the concepts of the invention, and is based upon FIG. 1A of the said '625 patent.

FIG. 10 shows how the components of the instant invention are assembled. Firstly sleeve 156 is inserted in bore 154 of head 152 and locked to head 152 by inserting a steel ball into aperture 160 until it engages slot 310. This permits sleeve 156 to move only through its desired travel path. Next the removable tool holder 100 is inserted in through the top of sleeve 156. The end 104 and collar 114 will extend below notched portion 305. The tool 20 is now inserted into the slot 112 of holder 100 aided in locating the mouth of slot 112 by chamfer 116. The tool portion 20 is pushed in as far as it can go guided by the slot 112 and the close fitting bore 154 of head 150. The tool portion 20 and the holder 100 can now be moved together to position the dental implement, made up of tool portion 20 and holder 100, at its desired location based upon the use to be made of the implement.

Figure 6:
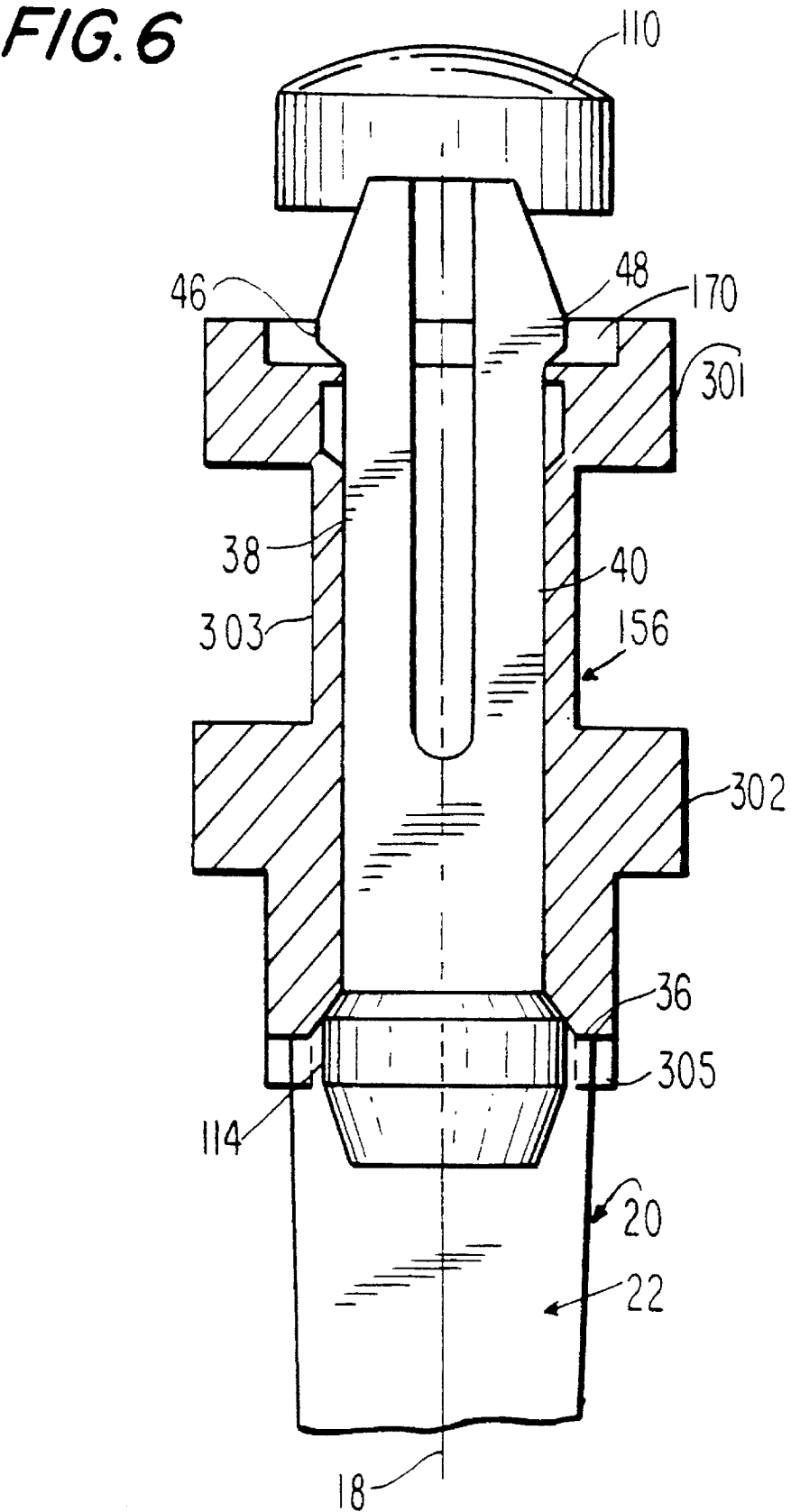
FIG. 6 is a front elevational view of the assembled dental implement according to the concepts of the invention, with a portion of the blade removed, and mounted within a sleeve, shown in section, of a dental handpiece set for reciprocating motion.

If it is desired to have the tool portion 20 move with sleeve 156 in reciprocating motion only, the implement is moved upwardly towards the top of the sheet in FIG. 6. In this manner the shoulders 36 of shank base 32 engage the notches of notched portion 305 which prevents rotation of tool portion 20. The protrusions 46, 48 extend into an annular recess 170 to prevent the movement of the tool portion 20 and holder 100 downwardly so that the shoulders 36 disengage from the notches of notched portion 305. The enlarged head 110 and the tapered portion adjacent end 108 of holder 100 are visible above the head 152.

Figure 7:
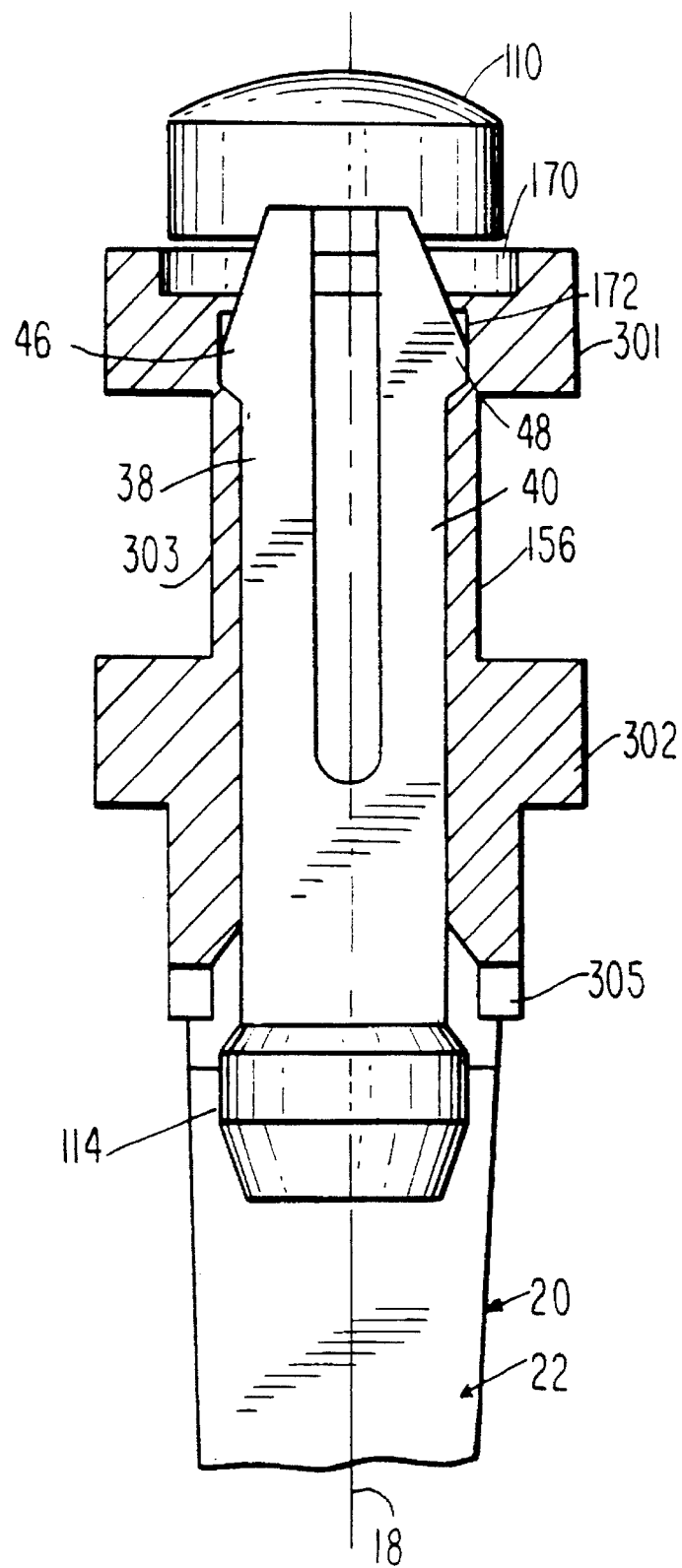
FIG. 7 is similar view to FIG. 6 but with the dental implement of the present invention set for reciprocating and rotary motion.

To permit the implement to move in reciprocating motion while allowing the tool portion 20 and holder 100 to be rotated, the enlarged head 110 is depressed towards the top of head 152 enough so that the shoulders 36 are free of the notches of the notched portion 305. The movement of head 110 causes the arms 38, 40 to approach axis 18 and allows movement of the implement downwardly in the bore of the sleeve 156 until protrusions 46, 48 are adjacent annular ring 172. At this point, the protrusions 46, 48 expand away from axis 18 into annular ring 172 (see FIG. 7). At this point shoulders 36 are free of the notches of notched portion 305. The implement is now free to be rotated as it is being used. The implement is not driven in a rotary manner but is free to be rotated if desired.

Figure 8:
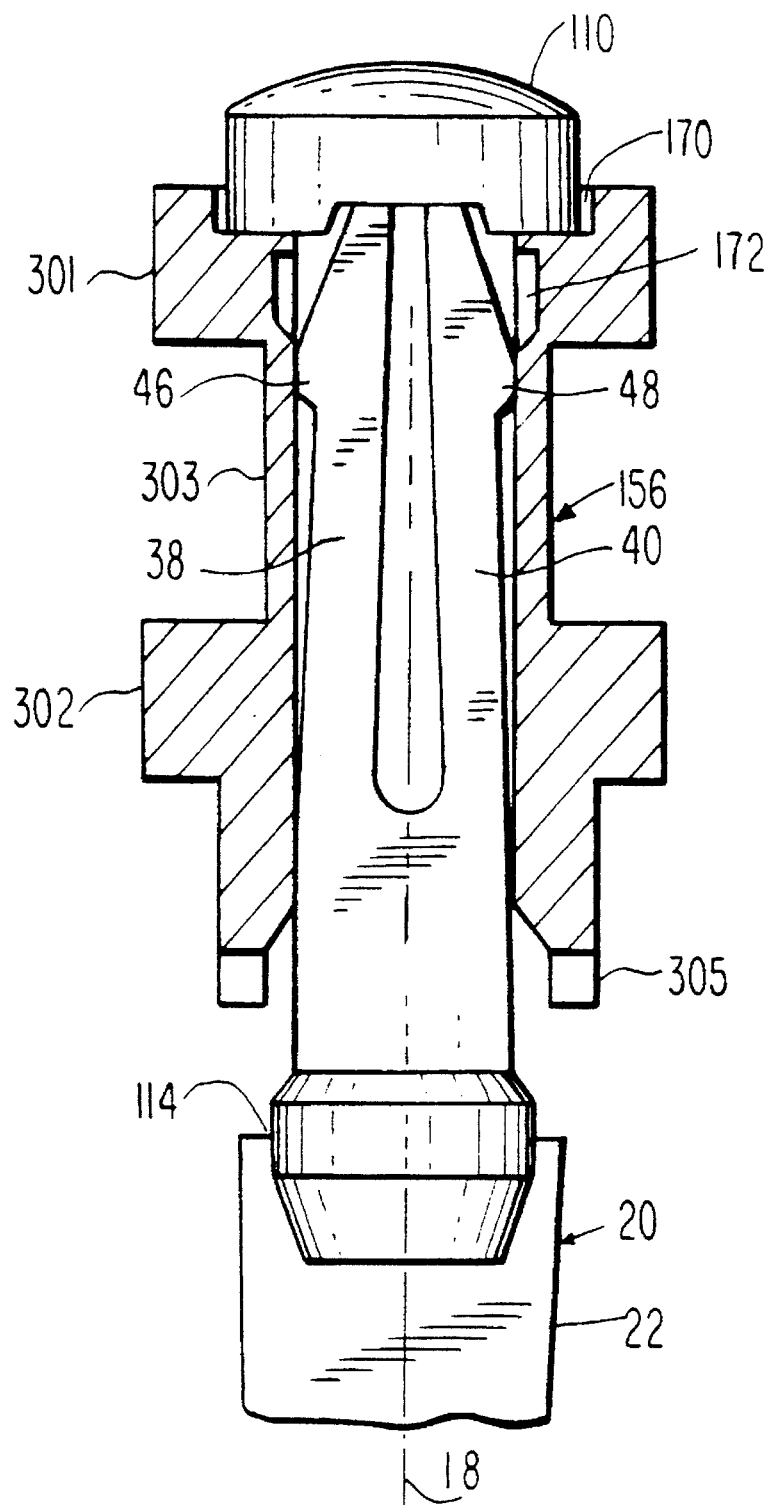
FIG. 8 is a similar view to FIGS. 6 and 7 but with the dental implement of the present invention set for removal of the tool blade.

To entirely remove the implement, the enlarged head 110 is pushed downwardly toward the bottom of FIG. 8 until the lower edge of the head 110 is in annular recess 170. This downward movement dislodges protrusions 46, 48 from annular ring 172 and places them in contact with the walls of the bore in sleeve 156. The protrusions 46, 48 are moved towards axis 18 by the combined effects of recess 112 of head 110 bearing on the inclined surfaces 58, 60 of arms 38 and 40 respectively, and inclined surfaces 50 and 52 of arms 38 and 40 respectively, against the bottom edge of annular ring 172. The tool portion 20 can now be pulled downwardly in FIG. 8 to free it from holder 100 and then holder 100 can be pulled upwardly in FIG. 8 to free it from the bore of sleeve 156.

While there have been shown and described and pointed out the fundamental novel features of the invention as applied to the preferred embodiment, it will be understood that various omissions and substitutions and changes of the form and details of the device illustrated and in its operation may be made by those skilled in the art, without departing from the spirit of the invention.

The embodiment of the invention in which an exclusive property or privilege is claimed are defined as follows:

1. In a dental device comprising reciprocating drive means, a sleeve member operatively connected to the drive means for reciprocating motion and designed to retain a dental tool, and a dental tool having a flat shank and a blade portion and being retained in said sleeve, the improvement comprising: a removable holder having a generally cylindrical body portion extending from an open first end to a closed second end; a slot in said body portion to receive therein said flat shank of said dental tool, said removable holder operatively connected to said sleeve member to provide reciprocating motion to said dental tool.

2. A dental device as defined in claim 1, wherein the width of said slot is less than the thickness of said flat shank of said dental tool to frictionally engage said dental tool placed in said slot of said removable holder.

3. A dental device as defined in claim 1, wherein said removable holder has an enlarged head adjacent said closed second end.

4. A dental device as defined in claim 1, wherein said removable holder is operatively connected to said sleeve member by protrusions on said flat shank of said dental tool which extend through said slot and engage said sleeve member.

5. A dental device as defined in claim 4, wherein said sleeve member has a first end and a second end and a series of grooves adjacent said second end to engage said flat blade portion of said dental tool to prevent rotation of said dental tool as said dental tool is subjected to reciprocating motion.

6. A dental device as defined in claim 4, wherein said sleeve means has at least two annular recesses in its interior surface to be selectively engaged by said protrusions on said flat shank of said dental tool, a first annular recess permitting said dental tool to move with a reciprocating motion only and the second annular recess permitting said dental tool to move with a reciprocating motion while permitting said dental tool to rotate with respect to said sleeve.

7. A dental device in accordance with claim 6, wherein the two annular recesses are axially distanced one from the other, wherein the dental tool is axially movable within the sleeve between the first annular recess located distal from the grooves, and the second annular recess located more proximal to the grooves.

8. A dental device as defined in claim 1, wherein said blade portion is flat.

9. A dental device as defined in claim 1, wherein said blade portion has a generally triangular cross-section.

10. A dental device as defined in claim 1, wherein said blade portion has a generally arcuate cross-section.

11. A dental device as defined in claim 1, wherein said blade has two straight marginal edges.

12. A dental device as defined in claim 1, wherein said blade has two marginal edges, at least one of which has a saw-tooth configuration.

13. A dental implement designed to be retained by a sleeve in a reciprocating dental implement drive means comprising:

tool means having a flat shank portion and a blade portion, said flat shank portion having a base portion coupled to said blade portion and two arms extending from said base portion to free ends;

each of said arms having an inside edge and an outside edge;

a protrusion on said outside edge of each of said arms, said protrusions extending outwardly from said arms away from the respective inner edges; and removable holder means to permit said tool means to be mounted in a reciprocating dental implement drive means, said removable holder means comprising an elongate cylindrical body extending from a first end to a second end about a central longitudinal axis;

said holder means having a slot extending from said first end through substantially all of said body along a diameter thereof; said slot being dimensioned so as to accept therein, with an interference fit, said flat shank and permitting said protrusions to extend beyond said holder body.

14. A dental implement as defined in claim 13, wherein said flat blade portion has two flat faces, at least one of said flat faces substantially covered with abrasive material.

15. A dental implement as defined in claim 13, wherein said shank portion comprises a relieved area between said arms adjacent said inside edges to permit said arms to be moved towards one another to change the spacing of said protrusions with respect to said central longitudinal axis and thereby change the type of drive applied to said dental implement by said reciprocating dental implement drive means.

16. A dental implement as defined in claim 15, wherein the free ends of each of said arms is tapered upwardly from said outside edge to said inside edge;

a cam surface in said holder means at the end of said slot, adjacent said second end, said cam having a shape complementary to said taper of the free ends of said arms, whereby the movement of said collect along said shank towards said blade causes said cam surface to engage said tapered surfaces of said arms and causes the spacing of said protrusions and said longitudinal axis to decrease and thereby separate said protrusions from contact with said reciprocating dental implement drive means thus ending drive of said dental implement by said reciprocating dental implement drive means.

17. A dental implement as defined in claim 13, wherein said blade portion is flat.

18. A dental implement as defined in claim 13, wherein said blade portion has a generally triangular cross-section.

19. A dental implement as defined in claim 13, wherein said blade portion has a generally arcuate cross-section.

20. A dental implement for abrasion, comprising:

a flat shank portion and a blade portion at least partially covered with abrasive material; and a collet member having an elongate body extending from a first end to a second end about a central longitudinal axis;

said collet member having a slot extending from said first end through substantially all of said body along a diameter thereof; said slot being dimensioned so as to accept therein, with an interference fit, said flat shank.

21. A dental implement as defined in claim 20, wherein said flat shank portion has a base portion coupled to said blade portion and two arms extending from said base portion to free ends;

each of said arms having an inside edge and an outside edge;

a protrusion on said outside edge of each of said arms, said protrusions extending outwardly from said arms away from the respective inner edges.

22. A dental implement as defined in claim 21, wherein said shank portion comprises a relieved area between said arms adjacent said inside edges to permit said arms inside edges to be moved towards one another to change the spacing of said protrusions with respect to a central longitudinal axis extending through the length of said dental implement.

23. A dental implement as defined in claim 22, wherein the free ends of each of said arms is tapered upwardly from said outside edge to said inside edge whereby a tool having a complementary taper to said free ends can be applied to said free ends of said arms to control the spacing of said protrusions with respect to said central longitudinal axis.

24. A dental implement as defined in claim 20, further comprising:

a blade portion having a generally triangular cross-section having at least two flat faces, said at least two flat faces substantially covered with abrasive material.

25. A dental implement as defined in claim 20, further comprising:

a blade portion having a generally arcuate cross-section with a curved outer face, said outer face substantially covered with abrasive material.

26. The dental implement of claim 20, wherein the blade portion is flat.

27. A dental implement for abrasion, comprising:

a flat tool portion having a flat shank portion and a flat blade portion having two flat faces, at least one of said flat faces substantially covered with abrasive material; and a collet member having an elongate cylindrical body extending from a first end to a second end about a central longitudinal axis;

said collet member having a slot extending from said first end through substantially all of said body along a diameter thereof; said slot being dimensioned so as to accept therein, with an interference fit, said flat shank.

28. A dental implement as defined in claim 25, wherein said flat shank portion has a base portion coupled to said blade portion and two arms extending from said base portion to free ends;

each of said arms having an inside edge and an outside edge;

a protrusion on said outside edge of each of said arms, said protrusions extending outwardly from said arms away form the respective inner edges;

said protrusions extending beyond the outer surface of said collet when said flat shank is positioned in said slot of said collet.

29. A dental implement as defined in claim 28, wherein said shank portion comprises a relieved area between said arms adjacent said inside edges to permit said arms inside edges to be moved towards one another to change the spacing of said protrusions with respect to said central longitudinal axis.

30. A dental implement as defined in claim 29, wherein the free ends of each of said arms is tapered upwardly from said outside edge to said inside edge;

a cam surface in said collet at the end of said slot, adjacent said second end, said cam having a shape complementary to said taper of the free ends of said arms, whereby the movement of said collet along said shank towards said blade causes said cam surface to engage said tapered surfaces of said arms and causes the spacing between said protrusions and said longitudinal axis to decrease.

31. A dental implement as defined in claim 30, wherein said collet further comprises an enlarged head at said second end and said portion of said collet immediately adjacent said enlarged head is inwardly tapered to where said enlarged head joins said collet;

said protrusions extending out of said collet at said inwardly tapered portion.

* * * * *